United States Patent
Nishigishi (10) Patent No.: US 10,143,575 B2
(45) Date of Patent: Dec. 4, 2018

(54) GUIDE WIRE

(71) Applicant: ASAHI INTECC CO., LTD., Nagoya-shi, Aichi (JP)

(72) Inventor: Makoto Nishigishi, Owariasahi (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 385 days.

(21) Appl. No.: 14/820,167

(22) Filed: Aug. 6, 2015

(65) Prior Publication Data

US 2016/0113793 A1 Apr. 28, 2016

(30) Foreign Application Priority Data

Oct. 22, 2014 (JP) ................................. 2014-214960

(51) Int. Cl.
*A61F 2/06* (2013.01)
*A61F 2/95* (2013.01)
(Continued)

(52) U.S. Cl.
CPC ................ *A61F 2/95* (2013.01); *A61F 2/966* (2013.01); *A61M 25/09* (2013.01);
(Continued)

(58) Field of Classification Search
CPC .... A61F 2/95; A61F 2/966; A61F 2002/9511; A61F 2002/9534; A61M 25/09; A61M 2025/09083; A61M 2025/09175
See application file for complete search history.

(56) References Cited

U.S. PATENT DOCUMENTS 4,925,445 A * 5/1990 Sakamoto ............. A61L 31/022
600/585
5,345,945 A * 9/1994 Hodgson ......... A61M 25/09033
600/433

(Continued)

FOREIGN PATENT DOCUMENTS

CN 101479006 A 7/2009
CN 102430184 A 5/2012
(Continued)

OTHER PUBLICATIONS

Feb. 24, 2016 Search Report issued in European Patent Application No. EP 15 189 471.4.
(Continued)

*Primary Examiner* — Son Dang
(74) *Attorney, Agent, or Firm* — Oliff PLC (57) ABSTRACT

A guide wire may include a core shaft and an external coil body covering a distal portion of the core shaft. The external coil body includes a first coil portion and a second coil portion that is distal to the first coil portion. An outside diameter of the second coil portion is smaller than an outside diameter of the first coil portion. Similarly, the guide wire may include a core shaft, a first external coil body, and a second external coil body. An outside diameter of the second external coil body is smaller than an outside diameter of the first external coil body. The external coil body or first and second external coil bodies enable the performance of a pushing-out operation and a drawing-in operation of the stent; yet, the flexibility of the guide wire is maintained.

3 Claims, 6 Drawing Sheets

(51) Int. Cl.
*A61F 2/966* (2013.01)
*A61M 25/09* (2006.01)

(52) U.S. Cl.
CPC .............. *A61F 2002/9511* (2013.01); *A61F 2002/9534* (2013.01); *A61M 2025/09083* (2013.01); *A61M 2025/09175* (2013.01)

(56) References Cited

U.S. PATENT DOCUMENTS

| | | | | |
|---|---|---|---|---|
| 5,766,202 | A * | 6/1998 | Jones | A61M 29/00 604/270 |
| 6,063,111 | A * | 5/2000 | Hieshima | A61B 17/12022 606/191 |
| 6,356,791 | B1 * | 3/2002 | Westlund | A61M 25/09 607/115 |
| 6,833,003 | B2 * | 12/2004 | Jones | A61F 2/95 623/1.11 |
| 7,025,734 | B1 * | 4/2006 | Ellis | A61B 5/14542 600/345 |
| 7,771,463 | B2 * | 8/2010 | Ton | A61F 2/88 623/1.11 |
| 8,236,042 | B2 * | 8/2012 | Berez | A61B 17/12022 623/1.11 |
| 8,267,985 | B2 | 9/2012 | Garcia et al. | |
| 2004/0059407 | A1 * | 3/2004 | Escamilla | A61B 17/12022 623/1.12 |
| 2004/0143240 | A1 * | 7/2004 | Armstrong | A61M 25/00 604/528 |
| 2005/0255317 | A1 * | 11/2005 | Bavaro | A61B 5/1076 428/375 |
| 2006/0095213 | A1 | 5/2006 | Escamilla et al. | |
| 2006/0111769 | A1 * | 5/2006 | Murray | A61F 2/95 623/1.12 |
| 2006/0265047 | A1 * | 11/2006 | Dorn | A61F 2/95 623/1.12 |
| 2006/0271153 | A1 * | 11/2006 | Garcia | A61B 17/12022 623/1.11 |
| 2007/0060996 | A1 | 3/2007 | Goodin et al. | |
| 2008/0255654 | A1 | 10/2008 | Hebert et al. | |
| 2008/0281396 | A1 * | 11/2008 | Ishida | A61F 2/91 623/1.11 |
| 2008/0300667 | A1 * | 12/2008 | Hebert | A61F 2/95 623/1.11 |
| 2010/0318065 | A1 | 12/2010 | Miyata et al. | |
| 2012/0065623 | A1 * | 3/2012 | Nelson, III | A61M 25/09 604/528 |
| 2012/0226343 | A1 * | 9/2012 | Vo | A61F 2/95 623/1.12 |
| 2013/0006222 | A1 * | 1/2013 | Nabeshima | A61M 25/09 604/528 |
| 2013/0066413 | A1 | 3/2013 | Jin et al. | |
| 2014/0025151 | A1 * | 1/2014 | Gao | A61F 2/86 623/1.11 |

FOREIGN PATENT DOCUMENTS

| | | |
|---|---|---|
| EP | 1 400 219 A1 | 3/2004 |
| JP | 2009-507560 A | 2/2009 |
| JP | 2011-000188 A | 1/2011 |
| JP | 2013-521022 A | 6/2013 |

OTHER PUBLICATIONS

Apr. 17, 2018 Office Action issued in Japanese Patent Application No. 2014-214960.
Feb. 2, 2018 Office Action issued in Chinese Patent Application No. 201510507156.3.
Jul. 17, 2018 Office Action issued in Chinese Patent Application No. 201510507156.3.

* cited by examiner

FIG. 6 ves of ed embodiments of a guide wire

GUIDE WIRE

CROSS REFERENCE TO RELATED APPLICATION

This application claims priority to Japanese Application No. 2014-214960 filed on Oct. 22, 2014, the content of which is incorporated by reference herein in its entirety.

BACKGROUND

The disclosed embodiments relate to a medical device. Specifically, the disclosed embodiments relate to a guide wire for delivering a stent that is housed within a catheter.

In a stent-placement procedure, a stent is expanded at a diseased site (for example, an occlusion site of a blood vessel) so that the diseased site is expanded from the inside, restoring blood flow. In such a procedure, the stent, which is housed inside a catheter, is delivered to the diseased site by being pushed forward out of the catheter by a guide wire.

A conventional guide wire used in such a procedure includes a press member. The stent is advanced through the catheter by pushing the stent from its proximal end with the press member. The conventional guide wire enables the stent to be drawn back in the proximal direction (to the side close to the technician) by a frictional force between the stent and an abutting member that is provided at a distal portion of the press member (a portion on which the stent is mounted). See Japanese Unexamined Patent Application Publication No. 2013-521022 (Translation of PCT Application).

However, there is a problem in the conventional guide wire described above in that the flexibility of the guide wire is impaired by being provided with the press member and the abutting member. As a result, it is disadvantageously difficult to deliver the stent to an end of a tortuous blood vessel.

SUMMARY

The disclosed embodiments have been devised in response to the problems described above that are encountered in the conventional art, and an object of the disclosed embodiments is to provide a guide wire, which is used for delivering a stent, with excellent flexibility while maintaining the ability to draw the stent back inside a catheter.

In order to address the above problems, a guide wire of the disclosed embodiments employs the following configuration. The guide wire, which is capable of delivering a stent housed within a catheter to a diseased site, includes a core shaft and an external coil body or external coil bodies covering a distal portion of the core shaft. When multiple external coil bodies are used (that is, each external coil body is a separate member), a first external coil body abuts against a proximal end (rear end) of the stent inside the catheter, and a second external coil body is positioned distal to the first external coil body and abuts against an inner peripheral surface of the stent. When a single external coil body is used (that is, the external coil body is a single member), a first coil portion of the external coil body abuts against the proximal end of the stent inside the catheter, and a second coil portion of the external coil body that is distal to the first coil portion abuts against the inner peripheral surface of the stent. The first coil portion and the second coil portion are formed as a single member in an integrated manner.

In such a guide wire of the disclosed embodiments, since the first external coil body or first coil portion abuts against the proximal end of the stent and the second external coil body or second coil portion abuts against the inner peripheral surface of the stent, the stent can be pushed out of the catheter with the first external coil body or first coil portion, and the stent can be drawn back into the catheter by a frictional force between the second external coil body or second coil portion and the inner peripheral surface of the stent.

Note that in the guide wire of the disclosed embodiments, the first external coil body or first coil portion that pushes the stent and the second external coil body or second coil portion that draws the stent back are each configured by a coil. Accordingly, the flexibility of the guide wire can be maintained despite including members for performing a pushing-out operation and a drawing-in operation of the stent. This facilitates delivery of the stent to the end of a tortuous blood vessel.

BRIEF DESCRIPTION OF THE DRAWINGS

FIG. 2A illustrates a state in which the stent is advanced, and FIG. 2B illustrates a state in which the stent is retracted.

DETAILED DESCRIPTION OF EMBODIMENTS

Hereinafter, the disclosed embodiments of a guide wire will be described.

Figure 1:
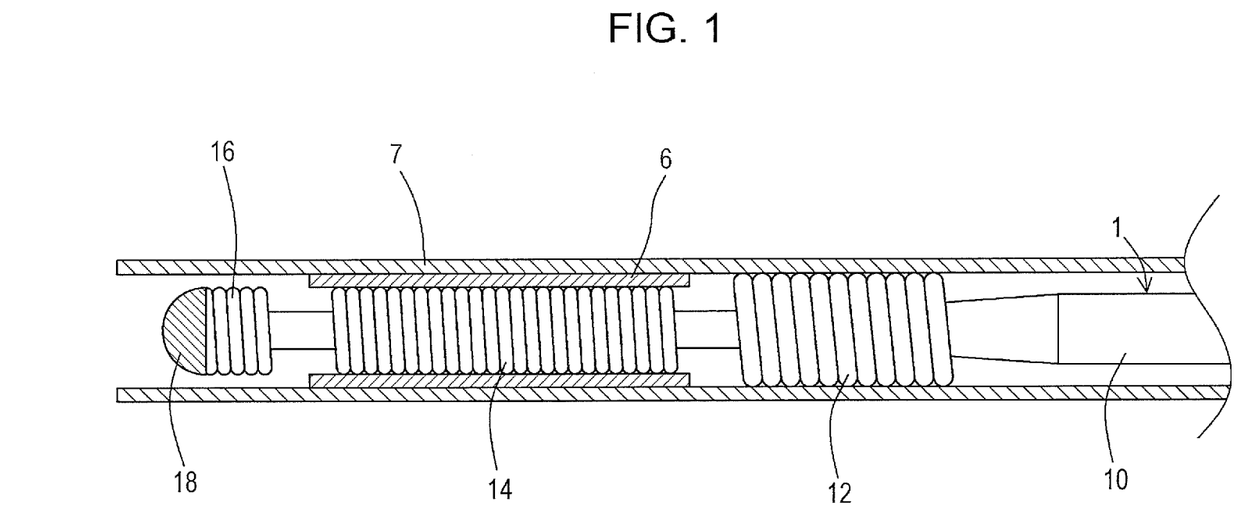
FIG. 1 is an explanatory drawing illustrating a configuration of a guide wire of the disclosed embodiments.

FIG. 1 is an explanatory drawing illustrating a configuration of a guide wire 1 of the disclosed embodiments. The guide wire 1 includes a core shaft 10 and three coil bodies (a first external coil body 12, a second external coil body 14, and a distal end coil body 16) that are provided on the distal portion of the core shaft 10 (distal being towards the left side of the drawing). In the guide wire 1, each of the three coil bodies is formed as a separate member. Furthermore, an outside diameter of the second external coil body 14 is smaller than an outside diameter of the first external coil body 12.

Among the three coil bodies, the first external coil body 12 is the most proximally disposed (towards the right side of the drawing), the second external coil body 14 is disposed distal to the first external coil body 12, and the distal end coil body 16 is disposed distal to the second external coil body 14 and at a distal end of the core shaft 10. The first external coil body 12 and the second external coil body 14 may each be formed of a radiolucent metal (stainless steel, for example). The distal end coil body 16 may be formed of a radiopaque metal (platinum, for example) so that the position of a distal end of the guide wire 1 can be perceived in a fluoroscopic image.

The first external coil body 12, the second external coil body 14, and the distal end coil body 16 are each joined to the core shaft 10 with a brazing material, an adhesive, or the like (not shown). As illustrated in FIG. 1, the guide wire 1 may also include a distal end brazing portion 18 that joins a distal end of the distal end coil body 16 and the distal end of the core shaft 10 to each other.

A self-expanding stent 6 is shown mounted onto the outer peripheral surface of the second external coil body 14. An assembly (a so-called stent delivery system) for delivering the stent 6 to an occlusion site of a blood vessel is configured by mounting the stent 6 onto the outer peripheral surface of the second external coil body 14 and by inserting the guide wire 1 with the mounted stent 6 into a bore (a lumen) of a catheter 7. In the above state, the outer peripheral surface of the second external coil body 14 abuts against an inner peripheral surface of the stent 6.

Figure 2A:
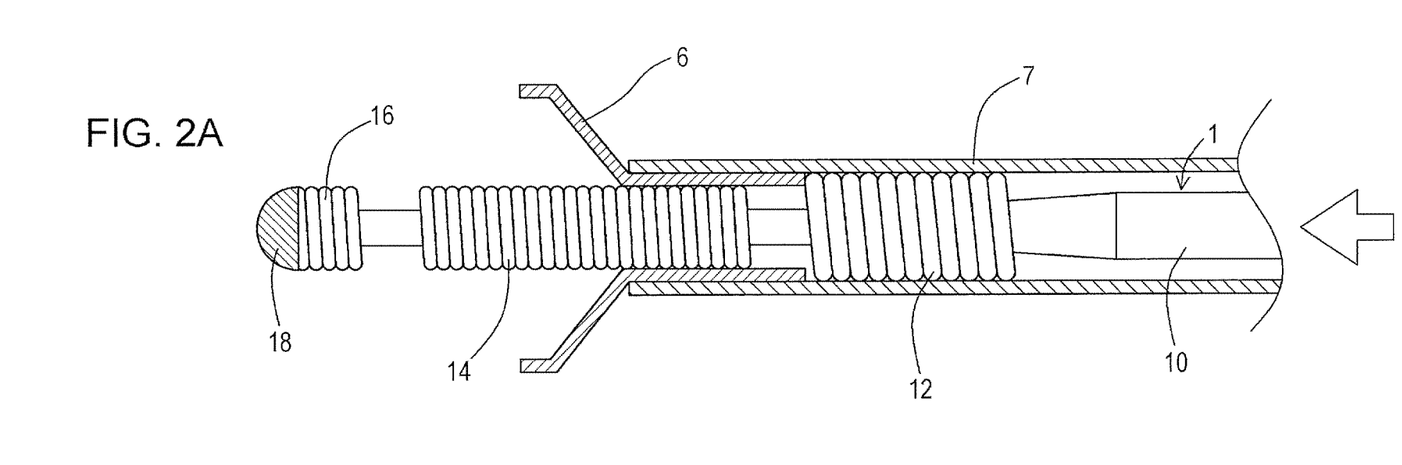
FIGS. 2A and 2B are explanatory drawings illustrating states in which a stent is advanced and retracted using the guide wire of FIG. 1.
Figure 2B:
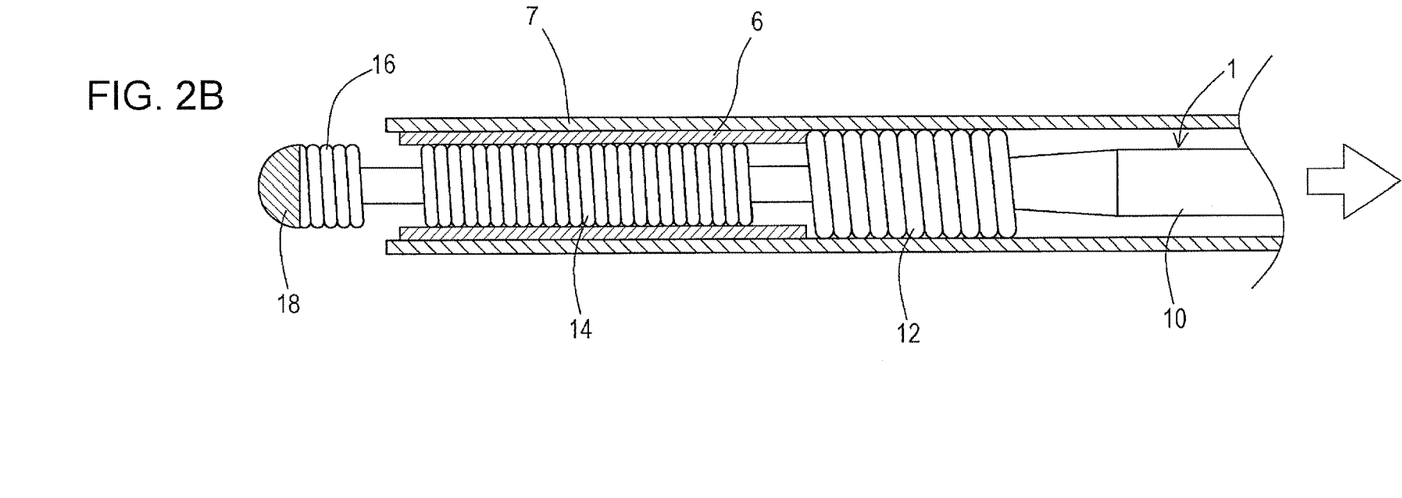

FIGS. 2A and 2B are explanatory drawings illustrating states in which the stent 6 is advanced and retracted using the guide wire 1 of FIG. 1. FIG. 2A illustrates a state in which the stent 6 is advanced, and FIG. 2B illustrates a state in which the stent 6 is retracted.

When the core shaft 10 of the guide wire 1 is pushed towards a distal end of the catheter 7 (the left side of the drawing) while the catheter 7 is held in place, the first external coil body 12 abuts against a proximal end of the stent 6, and the stent 6 is pushed by the first external coil body 12 and is moved towards the distal end of the catheter 7. When the stent 6 is pushed out of the distal end of the catheter 7, a portion of the stent 6 that is exposed to the outside of the catheter 7 expands by a self-restoring force (see FIG. 2A).

Furthermore, when the guide wire 1 is drawn back towards a proximal end of the catheter 7 (the right side of the drawing) while in a state illustrated in FIG. 2A (a state in which the portion of the stent 6 is exposed to the outside of the catheter 7), the stent 6 is moved towards the proximal end of the catheter 7 due to the frictional force between the stent 6 and the second external coil body 14, and is retrieved into the catheter 7 (see FIG. 2B).

In the above guide wire 1, since the stent 6 not only can be pushed out with the first external coil body 12 but also can be drawn back with the second external coil body 14, fine adjustment of the placing position of the stent 6 can be performed.

Furthermore, in the guide wire 1, the first external coil body 12 that pushes the stent 6 and the second external coil body 14 that draws the stent 6 back are each configured by a coil. Accordingly, the flexibility of the guide wire 1 can be maintained despite including these members for pushing out and drawing in the stent 6. This facilitates delivery of the stent 6 to an end of a tortuous blood vessel.

Figure 3:
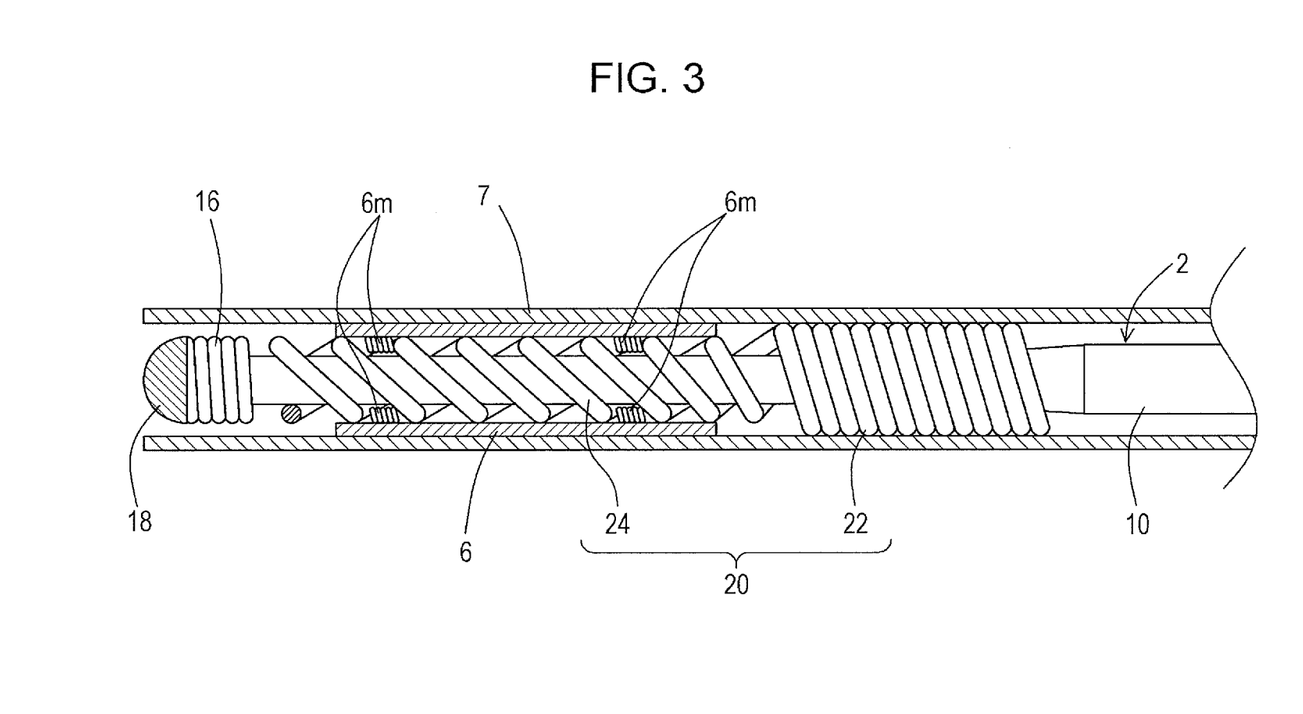
FIG. 3 is an explanatory drawing illustrating a configuration of a guide wire of the disclosed embodiments.

FIG. 3 is an explanatory drawing illustrating a configuration of a guide wire 2 of the disclosed embodiments. The guide wire 2 is different from the guide wire 1 described above in the following points. That is, an external coil body 20 is configured by a first coil portion 22 and a second coil portion 24 that are formed with a plurality of wires in an integrated manner. That is, the external coil body 20 is a single member formed by winding the plurality of wires. The second coil portion 24 is distal to the first coil portion 22. Furthermore, the first coil portion 22 is formed in a densely (tightly) wound manner, and the second coil portion 24 is formed in a sparsely (loosely) wound manner. An outside diameter of the second coil portion 24 is smaller than an outside diameter of the first coil portion 22.

Note that in the present description, "densely wound" refers to a state in which the adjacent wires of the coil are in contact with each other, and "sparsely wound" refers to a state in which the adjacent wires of the coil are not in contact with each other (that is, there are gaps between adjacent wires).

Note that the first coil portion 22 and the second coil portion 24 may be formed in an integrated manner using a single wire (that is, by winding a single wire).

Points other than the above are similar to the guide wire 1. The guide wire 2 is provided with the distal end coil body 16 at the distal end of the core shaft 10, and the distal end of the core shaft 10 and the distal end of the distal end coil body 16 are joined to each other with the distal end brazing portion 18. Furthermore, in a state in which the stent 6 is mounted onto an outer peripheral surface of the second coil portion 24 and in which the guide wire 2 and the stent 6 are inserted into the catheter 7, the outer peripheral surface of the second coil portion 24 abuts against the inner peripheral surface of the stent 6. Additionally, when the core shaft 10 of the guide wire 2 is pushed towards a distal end of the catheter 7 (the left side of the drawing) while the catheter 7 is held in place, the first coil portion 22 abuts against the proximal end of the stent 6, and the stent 6 is pushed by the first coil portion 22 and is moved towards the distal end of the catheter. 7.

In the above guide wire 2, since the first coil portion 22 and the second coil portion 24 are formed in an integrated manner with the plurality of wires, the guide wire 2 that is capable of pushing out and drawing in the stent 6 and that is flexible can be readily fabricated.

Furthermore, since the first coil portion 22 is densely wound, a force for pushing the stent 6 can be sufficiently obtained. Furthermore, since the second coil portion 24 is sparsely wound, the second coil portion 24 can be readily engaged with the stent 6.

Additionally, since the first coil portion 22 and the second coil portion 24 are formed by the plurality of wires, expansion and contraction of the first coil portion 22 and the second coil portion 24 are suppressed. As a result, the second coil portion 24 can be maintained in a sparsely wound state (a state in which engagement with the stent is facilitated).

Furthermore, since the second coil portion 24 is sparsely wound, an additional effect as below can be obtained. That is, as illustrated in FIG. 3, in a case in which attachments (marker coils 6*m*) protrude from the inner peripheral surface of the stent 6, the marker coils 6*m* can be engaged between the wires of the second coil portion 24. As a result, the stent 6 can be drawn back easily.

Figure 4:
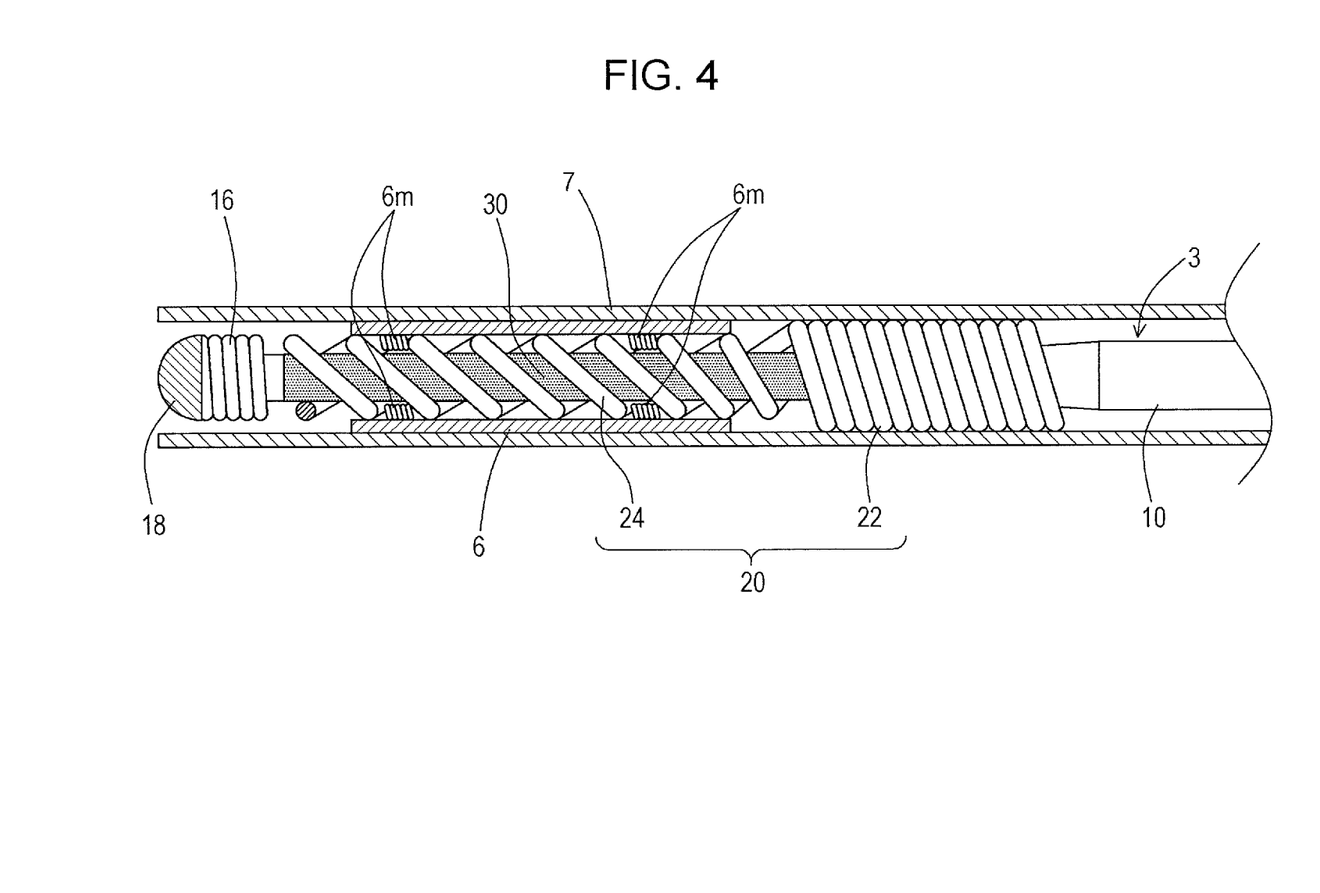
FIG. 4 is an explanatory drawing illustrating a configuration of a guide wire of the disclosed embodiments.

FIG. 4 is an explanatory drawing illustrating a configuration of a guide wire 3 of the disclosed embodiments. The guide wire 3 is different from the guide wire 2 described above in the following points. That is, a friction member 30 is provided between the external coil body 20, which is formed of the first coil portion 22 and the second coil portion 24, and the core shaft 10. A thin rubber sheet may be used as the friction member 30.

Note that while the friction member 30 may be provided between the external coil body 20 and the core shaft 10 of the guide wire 2 (as exemplified in FIG. 4), the friction member 30 may be provided between the first external coil body 12 and the second external coil body 14, and the core shaft 10 of the guide wire 1 described above (not shown). However, as described above with respect to FIG. 3, from the viewpoint of facilitating fabrication of the guide wire, it is desirable that the first coil portion 22 and the second coil portion 24 are formed in an integral manner as the external coil body 20, illustrated in FIG. 4.

Points other than the above are similar to the guide wire 2. In other words, the distal end coil body 16 is provided at the distal end of the core shaft 10, and the distal end of the core shaft 10 and the distal end of the distal end coil body 16 are joined to each other with the distal end brazing portion 18. Furthermore, in a state in which the stent 6 is mounted onto the outer peripheral surface of the second coil portion 24 and in which the guide wire 3 and the stent 6 are inserted into the catheter 7, the outer peripheral surface of the second coil portion 24 abuts against the inner peripheral surface of the stent 6.

In the above guide wire 3, since the friction member 30 is provided between the external coil body 20 and the core shaft 10, the position of the external coil body 20 can be prevented from being displaced with respect to the core shaft 10. Accordingly, a force pushing and drawing back the stent 6 can be sufficiently obtained.

Furthermore, when the second coil portion 24 is formed in a sparsely wound manner, the movement of the wires forming the second coil portion 24 on the core shaft 10 is restricted by the friction member 30 and, accordingly, the sparsely wound state can be maintained. As a result, the second coil portion 24 can be reliably engaged with the stent 6 to the draw the stent 6 back into the catheter 7.

Figure 5:
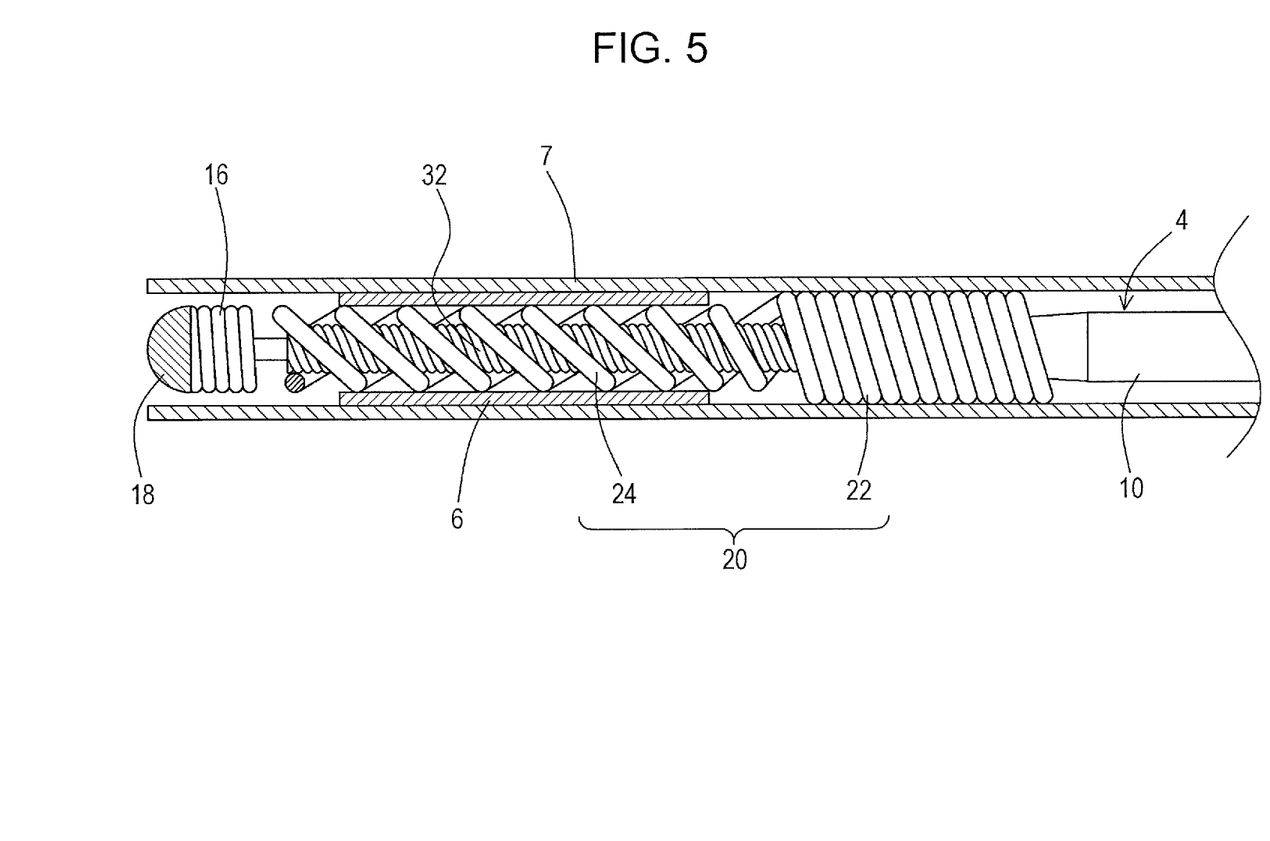
FIG. 5 is an explanatory drawing illustrating a configuration of a guide wire of the disclosed embodiments.

FIG. 5 is an explanatory drawing illustrating a configuration of a guide wire 4 of the disclosed embodiments. The guide wire 4 is different from the guide wire 3 described above in the following points. That is, a friction member between the external coil body 20, which is formed of the first coil portion 22 and the second coil portion 24, and the core shaft 10 is configured by an internal coil body 32. The wire diameter of the wire of the internal coil body 32 is smaller than the wire diameter of the wire(s) of the external coil body 20. Furthermore, in FIG. 5, the winding direction of the wire of the internal coil body 32 and the winding direction of the wire(s) of the external coil body 20 are the same.

Note that while the internal coil body 32 may be provided between the external coil body 20 and the core shaft 10 of the guide wire 2 (as exemplified in FIG. 5), the internal coil body 32 may be provided between the first external coil body 12 and the second external coil body 14, and the core shaft 10 of the guide wire 1 described above (not shown).

Points other than the above are similar to the guide wire 3. That is, the distal end coil body 16 is provided at the distal end of the core shaft 10, and the distal end of the core shaft 10 and the distal end of the distal end coil body 16 are joined to each other with the distal end brazing portion 18. Furthermore, in a state in which the stent 6 is mounted onto the outer peripheral surface of the second coil portion 24 and in which the guide wire 4 and the stent 6 are inserted into the catheter 7, the outer peripheral surface of the second coil portion 24 abuts against the inner peripheral surface of the stent 6.

In the above guide wire 4, since the friction member is a coil body (the internal coil body 32) and the internal coil body 32 is formed of a wire that has a diameter that is smaller than the diameter of the wire(s) of the external coil body 20, in addition to the effects of the disclosed embodiments described above, the flexibility of the guide wire 4 can be maintained even when the fixing member is provided. As a result, the stent 6 can be reliably delivered to the end of meandering tortuous blood vessel.

Figure 6:
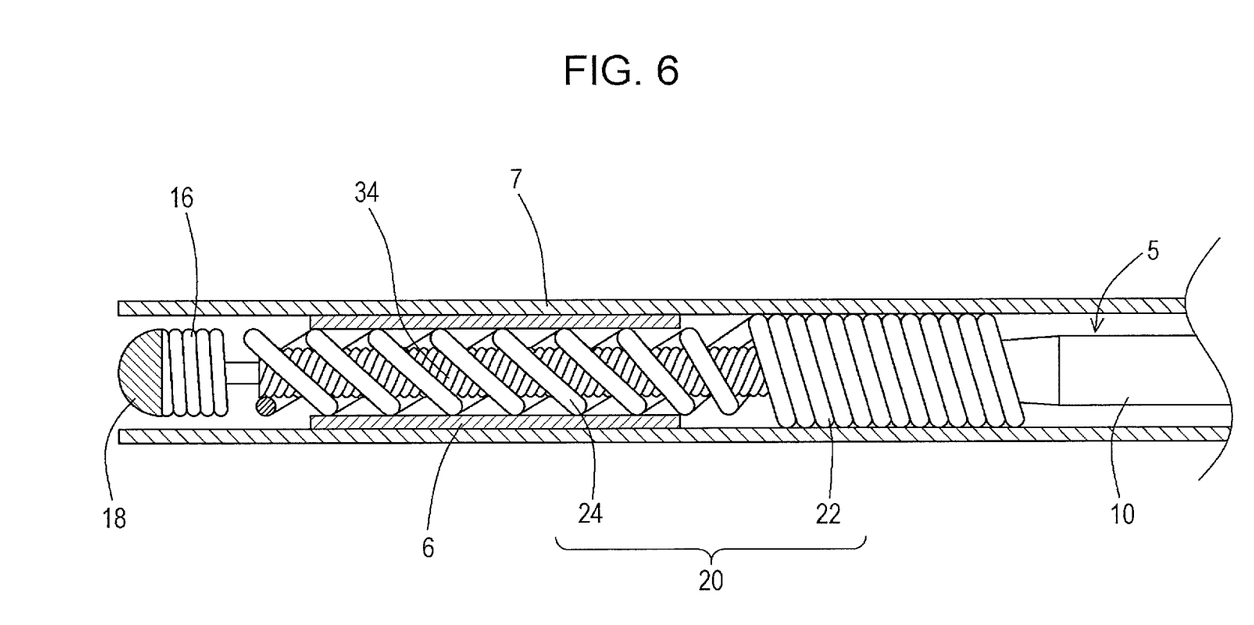
FIG. 6 is an explanatory drawing illustrating a configuration of a guide wire of the disclosed embodiments.

FIG. 6 is an explanatory drawing illustrating a configuration of a guide wire 5 of the disclosed embodiments. The guide wire 5 is different from the guide wire 4 described above in the following points. That is, an internal coil body 34 is provided between the external coil body 20, which is formed of the first coil portion 22 and the second coil portion 24, and the core shaft 10, and the winding direction of the wire of the internal coil body 34 is opposite to the winding direction of the wire(s) of the external coil body 20.

Points other than the above are similar to the guide wire 4. In other words, the distal end coil body 16 is provided at the distal end of the core shaft 10, and the distal end of the core shaft 10 and the distal end of the distal end coil body 16 are joined to each other with the distal end brazing portion 18. Furthermore, in a state in which the stent 6 is mounted onto the outer peripheral surface of the second coil portion 24 and in which the guide wire 4 and the stent 6 are inserted into the catheter 7, the outer peripheral surface of the second coil portion 24 abuts against the inner peripheral surface of the stent 6.

In the above guide wire 5, since the winding direction of the wire of the internal coil body 34 is opposite to the winding direction of the wire(s) of the external coil body 20, the frictional force between the external coil body 20 and the internal coil body 34 can be increased further. As a result, in addition to the effects of the various embodiments described above, positional displacement of the external coil body 20 with respect to the core shaft 10 can be even more reliably prevented.

While the guide wires 1-5 have been described above, the present disclosure is not limited to the embodiments described above and can be implemented in various manners. For example, description has been given above that, in the guide wires 1-5, the outside diameter of the second external coil body 14 is smaller than the outside diameter of the first external coil body 12 (see FIGS. 1 and 2), and the outside diameter of the second coil portion 24 is smaller than the diameter of the first coil portion 22 (see FIGS. 3 to 6). However, the outside diameters of the first external coil body 12 and the second external coil body 14, or of the first coil portion 22 and the second coil portion 24, may be substantially the same (not shown).

However, the outside diameter of the guide wire 1-5 having the stent 6 mounted on the outer peripheral surface of the second external coil body 14 or the second coil portion 24 can be made smaller when, as described above, the outside diameter of the second external coil body 14 or the second coil portion 24 is smaller than the outside diameter of first external coil body 12 or the first coil portion 22. As a result, a catheter 7 with a small outside diameter can be used and the stent 6 can be delivered to even a narrow blood vessel.

What is claimed is:

1. A guide wire configured to deliver a stent housed within a catheter, the guide wire comprising:
   a core shaft;
   an external coil body covering a distal portion of the core shaft and formed by winding one or more wires; and
   a friction member provided between the external coil body and the core shaft,
   wherein the external coil body includes a first coil portion and a second coil portion that is distal to the first coil portion, and an outside diameter of the second coil portion is smaller than an outside diameter of the first coil portion.

2. A stent delivery system comprising:
   the guide wire according to claim 1;
   the catheter; and
   the stent housed within the catheter and mounted onto an outer peripheral surface the second coil portion so that the outer peripheral surface of the second coil portion abuts against an inner peripheral surface of the stent.

3. The stent delivery system according to claim 2, wherein:
   attachments protrude from the inner peripheral surface of the stent, and the attachments are engaged in spaces formed between the one or more wires of the second coil portion.

* * * * *